(12) United States Patent
Rioux et al.

(10) Patent No.: US 10,603,393 B2
(45) Date of Patent: Mar. 31, 2020

(54) STERILIZABLE INDWELLING CATHETERS

(71) Applicant: Boston Scientific Scimed Inc., Maple Grove, MN (US)

(72) Inventors: Robert F. Rioux, Ashland, MA (US); Raymond Lareau, Westford, MA (US); Kristian DiMatteo, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1442 days.

(21) Appl. No.: 14/051,783

(22) Filed: Oct. 11, 2013

(65) Prior Publication Data
US 2014/0039418 A1 Feb. 6, 2014

Related U.S. Application Data

(63) Continuation of application No. 11/879,537, filed on Jul. 18, 2007, now Pat. No. 8,556,950.

(60) Provisional application No. 60/839,948, filed on Aug. 24, 2006.

(51) Int. Cl.
| | | |
|---|---|---|
| *A61L 2/08* | (2006.01) | |
| *A61L 29/14* | (2006.01) | |
| *A61L 29/04* | (2006.01) | |
| *A61L 2/10* | (2006.01) | |

(Continued)

(52) U.S. Cl.
CPC .............. *A61L 2/08* (2013.01); *A61L 2/084* (2013.01); *A61L 2/085* (2013.01); *A61L 2/10* (2013.01); *A61L 29/04* (2013.01); *A61L 29/08* (2013.01); *A61L 29/14* (2013.01); *A61M 25/0017* (2013.01); *A61M 2025/0056* (2013.01)

(58) Field of Classification Search
CPC .................................. A61B 18/20; A61N 5/06
USPC ...................................... 606/2–19; 607/88–94
See application file for complete search history.

(56) References Cited

U.S. PATENT DOCUMENTS

| | | | |
|---|---|---|---|
| 4,838,269 A | 6/1989 | Robinson et al. | |
| 5,053,423 A | 10/1991 | Liu | |
| 5,129,887 A | 7/1992 | Euteneuer et al. | |

(Continued)

FOREIGN PATENT DOCUMENTS

| | | |
|---|---|---|
| EP | 0670169 A2 | 6/1995 |
| WO | 02/102421 A1 | 12/2002 |
| WO | 01/87416 A1 | 11/2011 |

OTHER PUBLICATIONS

The Electromagnetic Spectrum, downloaded from hhtp:/library.thinkquest.org/27930/spectrum.htm on May 2, 2006.

(Continued)

*Primary Examiner* — Lynsey C Eiseman

(57) ABSTRACT

According to an aspect of the invention, an indwelling catheter is provided which comprises a catheter shaft. The catheter either comprises a light source or is adapted to receive light from a light source, and is configured such that light is transmitted from the light source into the catheter shaft. Moreover, the catheter shaft is formed of a polymeric material that transmits a quantity of light from the light source that is effective to inactivate microorganisms on a surface of the catheter shaft upon activation of the light source. For example, the light may inactivate the microorganisms directly or in conjunction with a photosensitizer. According to another aspect of the invention, a sterilization method is provided, which comprises activating the light source while the catheter is inserted in a subject.

16 Claims, 8 Drawing Sheets

(51) Int. Cl.
*A61L 29/08* (2006.01)
*A61M 25/00* (2006.01)

(56) References Cited

U.S. PATENT DOCUMENTS

| | | | |
|---|---|---|---|
| 5,229,431 | A | 7/1993 | Pinchuk |
| 5,240,675 | A | 8/1993 | Wilk et al. |
| 5,260,020 | A | 11/1993 | Wilk et al. |
| 5,334,171 | A | 8/1994 | Kaldany |
| 5,445,608 | A | 8/1995 | Chen et al. |
| 5,509,897 | A | 4/1996 | Twardowski et al. |
| 5,514,127 | A | 5/1996 | Shanks |
| 5,571,152 | A | 11/1996 | Chen et al. |
| 5,637,877 | A | 6/1997 | Sinofsky |
| 5,695,482 | A | 12/1997 | Kaldany |
| 5,702,754 | A | 12/1997 | Zhong |
| 5,817,072 | A | 10/1998 | Lampropoulos et al. |
| 5,830,526 | A | 11/1998 | Wilson et al. |
| 5,855,203 | A * | 1/1999 | Matter ............... A61L 2/10 128/207.14 |
| 6,030,411 | A | 2/2000 | Lawandy |
| 6,213,995 | B1 | 4/2001 | Steen et al. |
| 6,273,404 | B1 | 8/2001 | Holman et al. |
| 6,280,423 | B1 | 8/2001 | Davey et al. |
| 6,461,568 | B1 | 10/2002 | Eckhardt |
| 6,461,569 | B1 * | 10/2002 | Boudreaux ............... A61L 2/10 422/24 |
| 6,551,346 | B2 | 4/2003 | Crossley |
| 6,645,230 | B2 | 11/2003 | Whitehurst |
| 6,693,093 | B2 | 2/2004 | Chowdhary et al. |
| 6,730,113 | B2 | 5/2004 | Eckhardt et al. |
| 6,819,951 | B2 | 11/2004 | Patel et al. |
| 6,969,381 | B2 | 11/2005 | Voorhees |
| 2001/0047195 | A1 | 11/2001 | Crossley |
| 2002/0082559 | A1 | 6/2002 | Chang et al. |
| 2002/0165594 | A1 | 11/2002 | Biel |
| 2003/0017073 | A1 | 1/2003 | Eckhardt et al. |
| 2003/0194433 | A1 | 11/2003 | Hei et al. |
| 2004/0034398 | A1 | 2/2004 | Eckhardt et al. |
| 2004/0073171 | A1 | 4/2004 | Rogers et al. |
| 2004/0131863 | A1 | 7/2004 | Belliveau et al. |
| 2005/0240080 | A1 | 10/2005 | Diekmann et al. |
| 2006/0004317 | A1 * | 1/2006 | Mauge ............... A61M 27/006 604/8 |

OTHER PUBLICATIONS

T.S. Gunasekera et al., "Responses of phylloplane yeasts to UV-B (290-320 nm) radiation: interspecific differences in sensitivity," Mycological Research, 101, 1997, pp. 779-785.

J. Shilke et al., "Sensitization of cariogenic bacteria to killing by laser light," Abstract 3631, Saturday, Mar. 9, 2002, San Diego Convention Center Exhibit Hall C.

L.M. Sheppard, "Novel LEDS Could Eliminate Bacteria," Technology World, Jul. 1999, 2 pages.

S.A. Weiss, "Lasers Aid in Bacterial Destruction," Technology World, Feb. 1998, 1 page.

M.Wilson, "Light-activated antimicrobial coating for the continuous disinfection of surfaces," Infect Control HOSP Epidemiol. Oct. 24, 2003, vol. 10, pp. 782-784.

J.A. Williams et al., "The photo-activated antibacterial action of toluidine blue O in a collagen matrix and in carious dentine," Caries Res., Nov.-Dec. 2004, 38, vol. 6, pp. 530-536.

A. Rasooly et al., "In Vitro antibacterial activities of phloxine B and other halogenated fluoresceins against methicillin-resistant *Staphylococcus aureus*," Antimicrob Agents Chemother. Nov. 2002, 46, vol. 11, pp. 3650-3653.

* cited by examiner

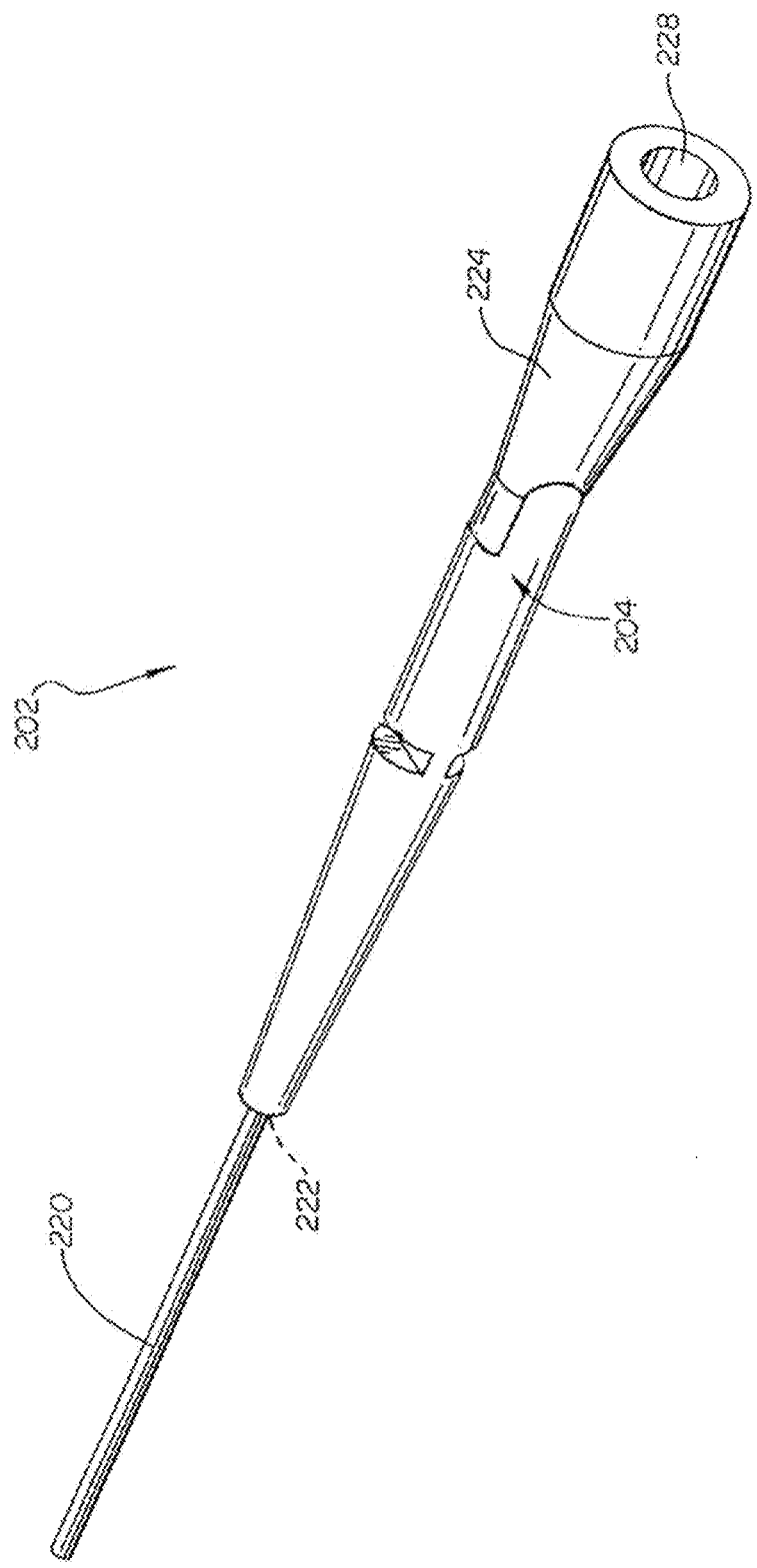
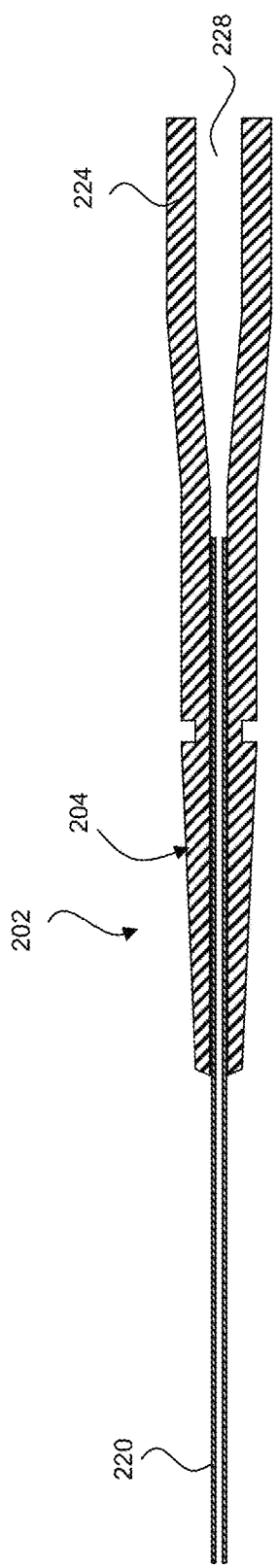
Fig. 1A
Fig. 1B

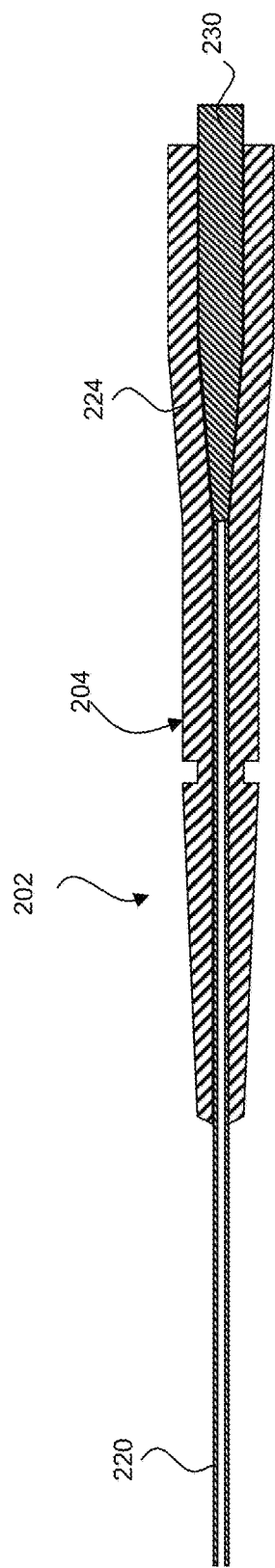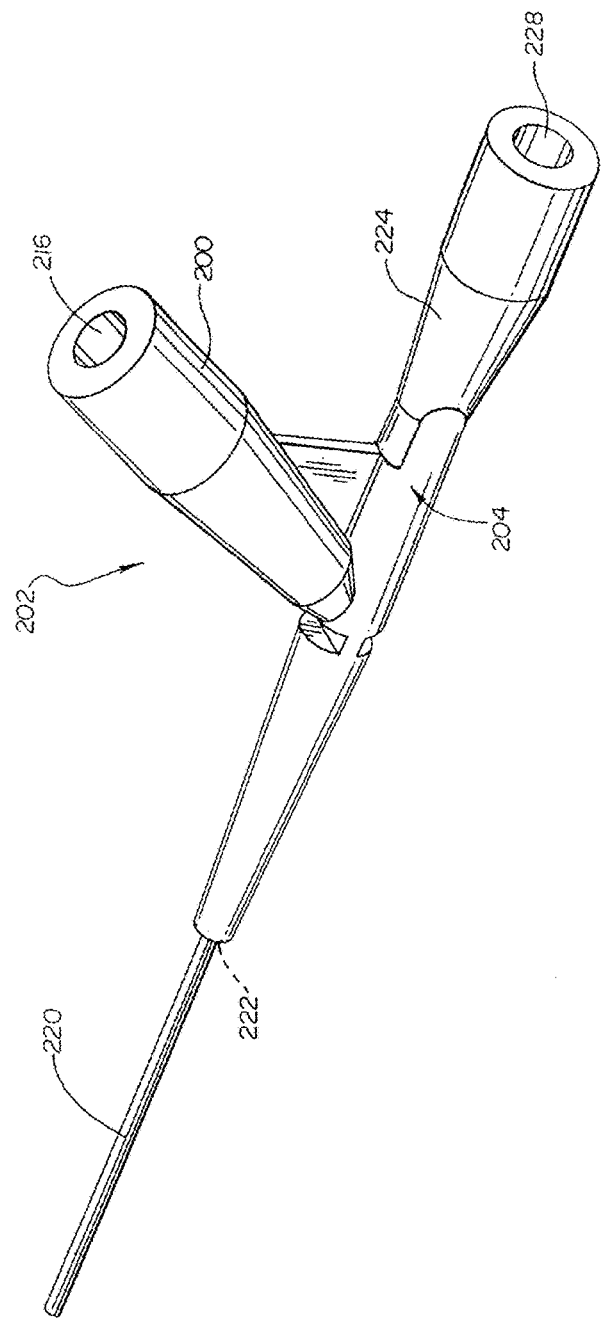

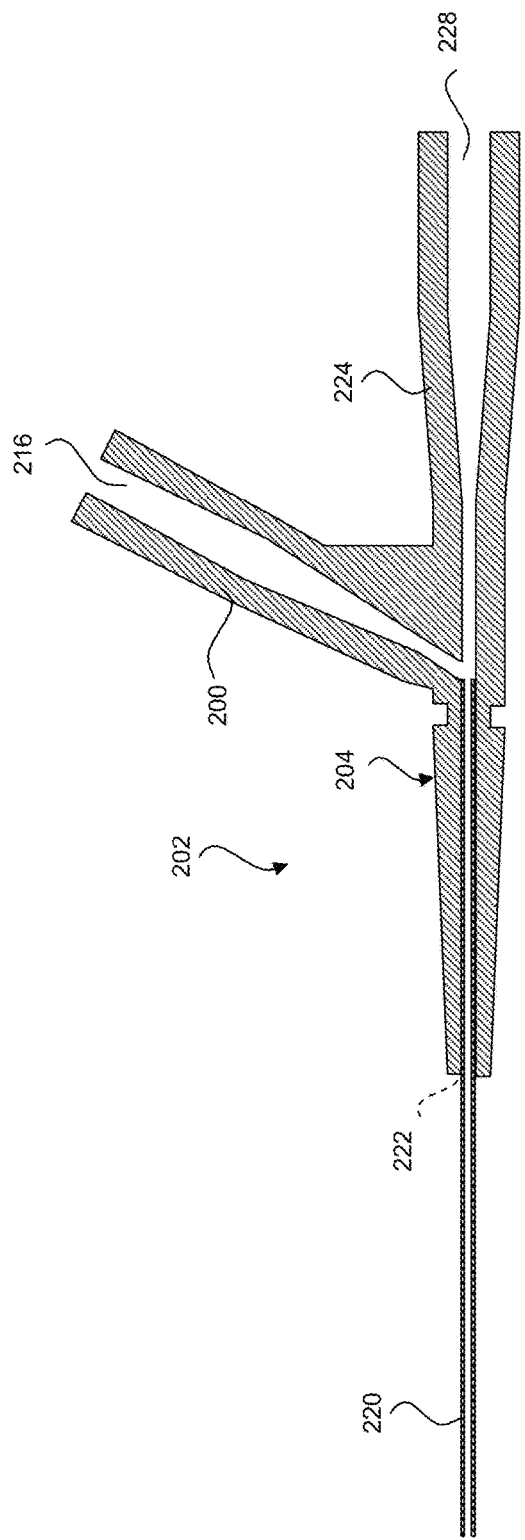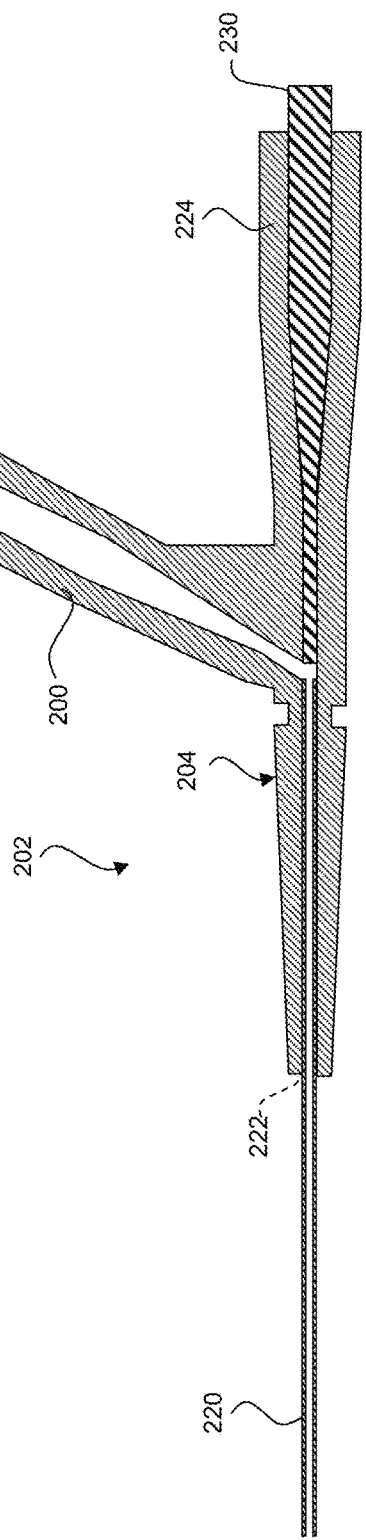

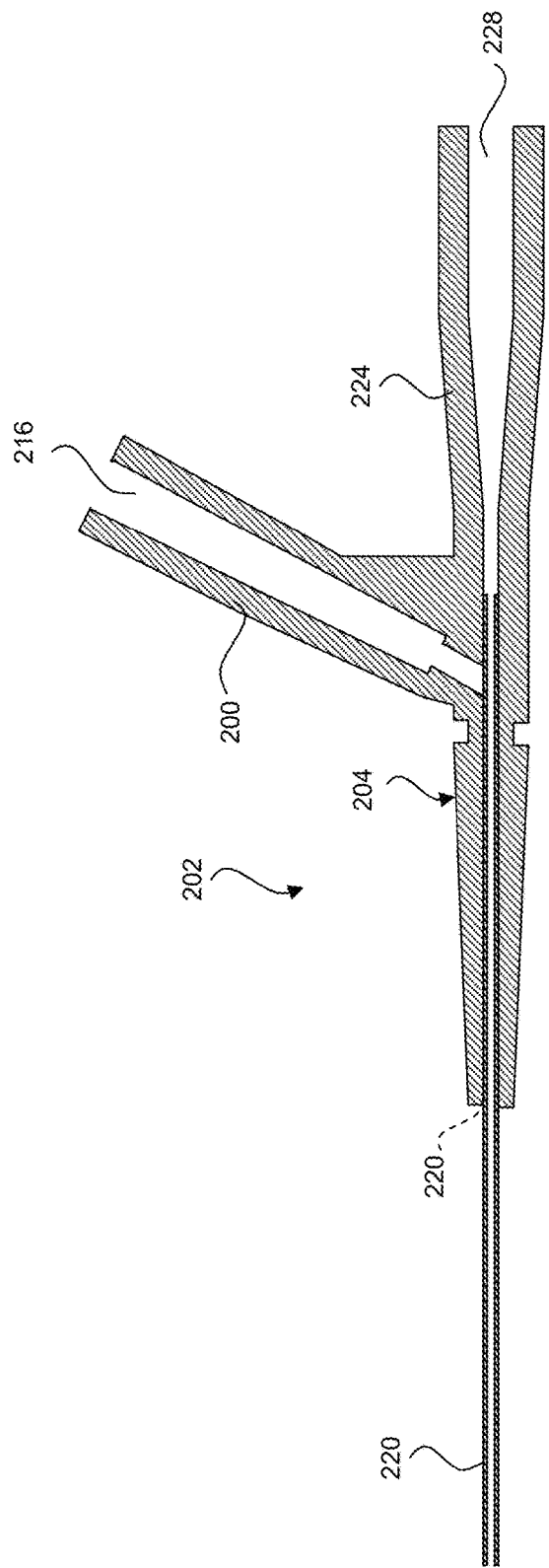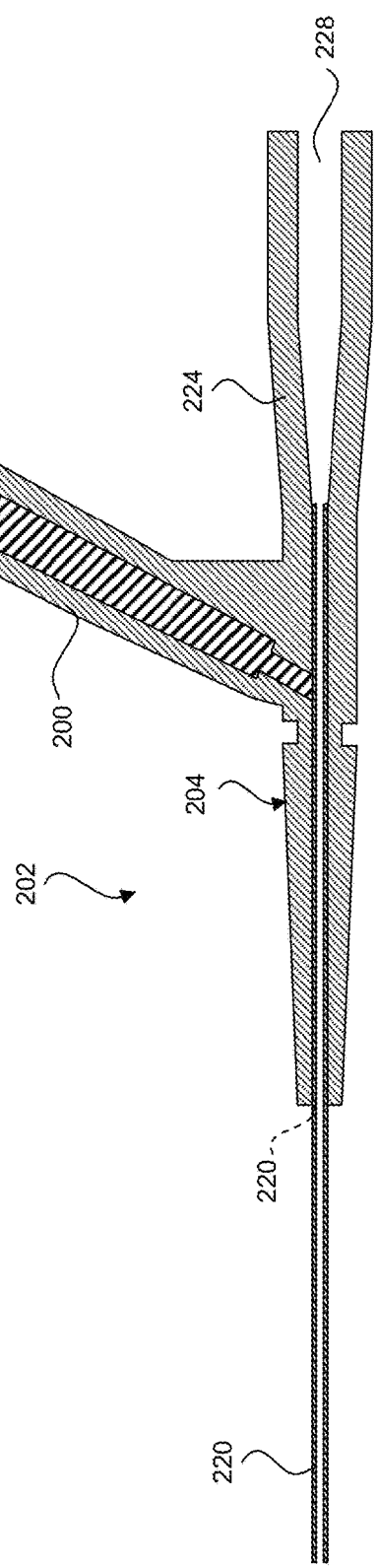

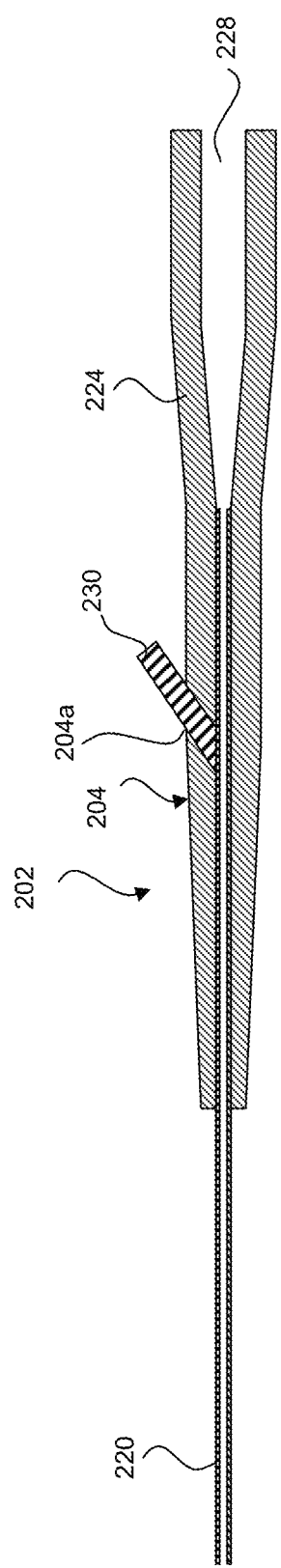
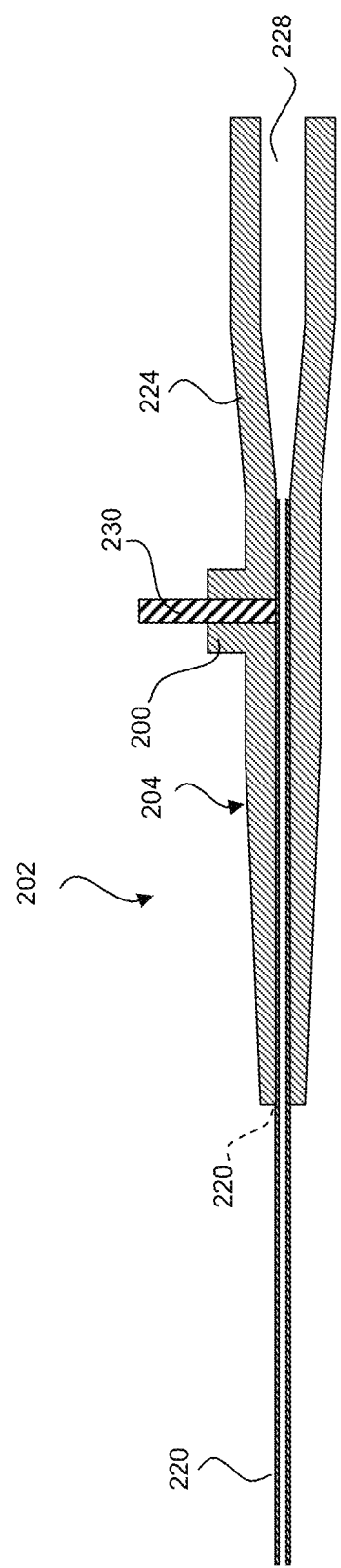

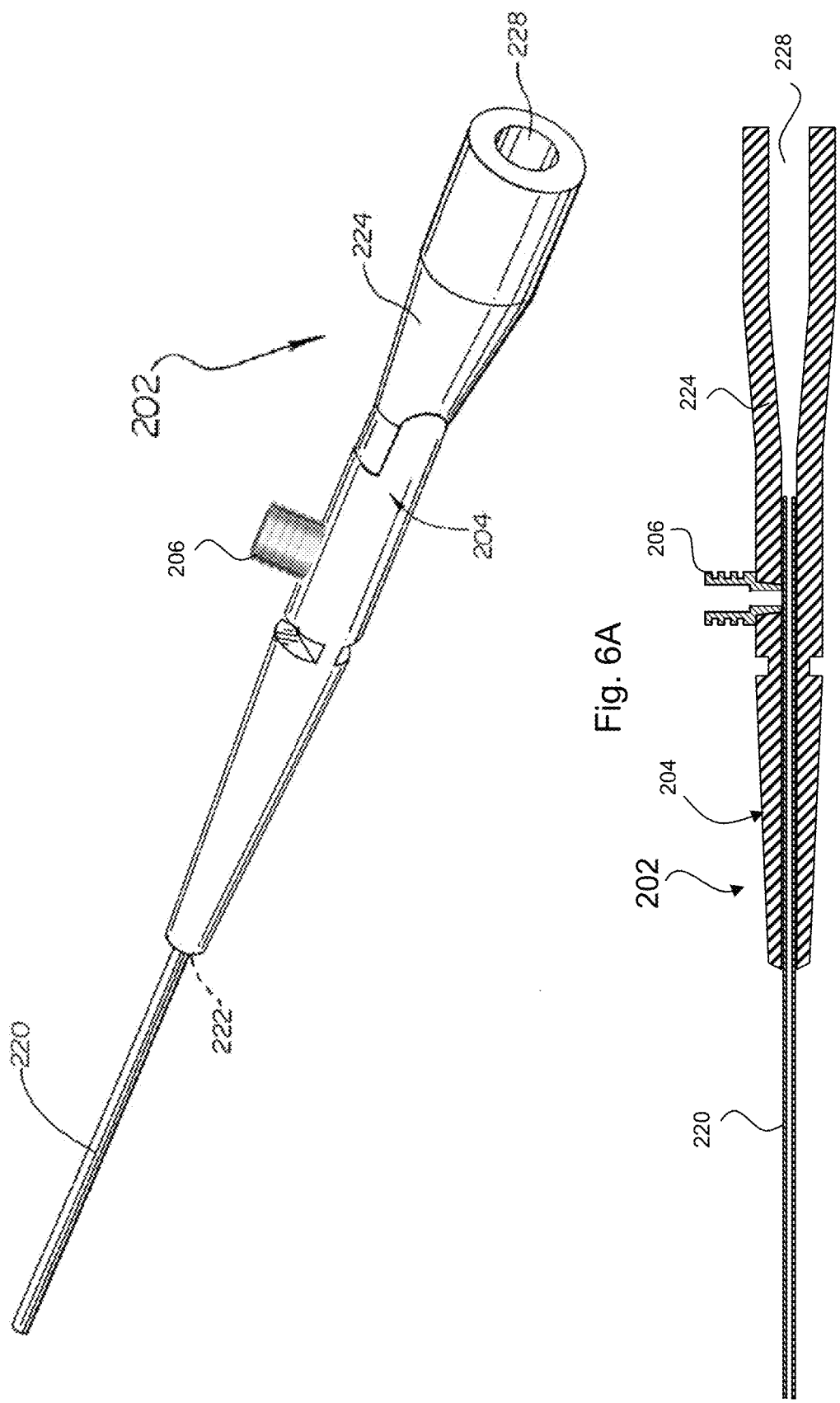

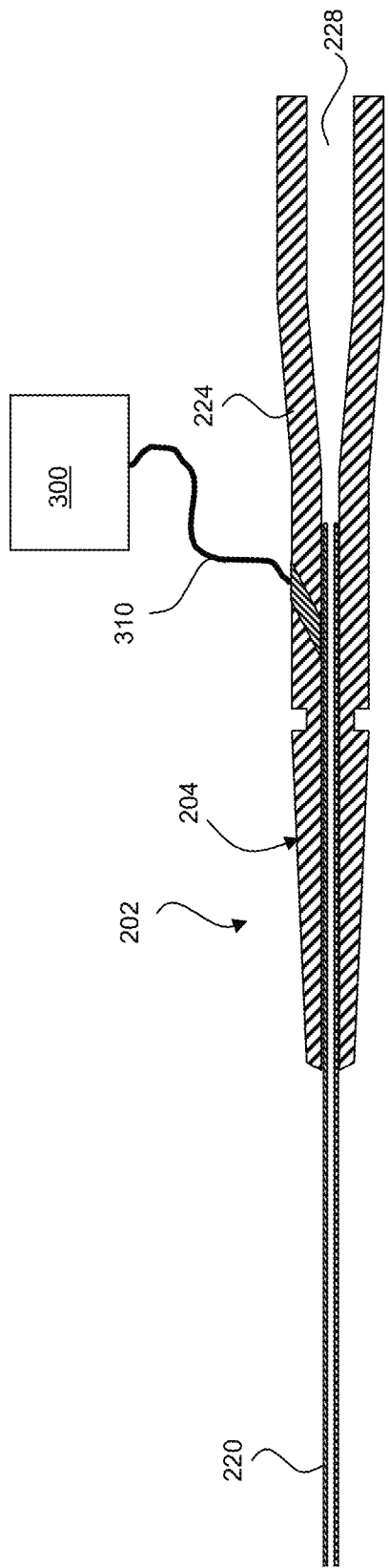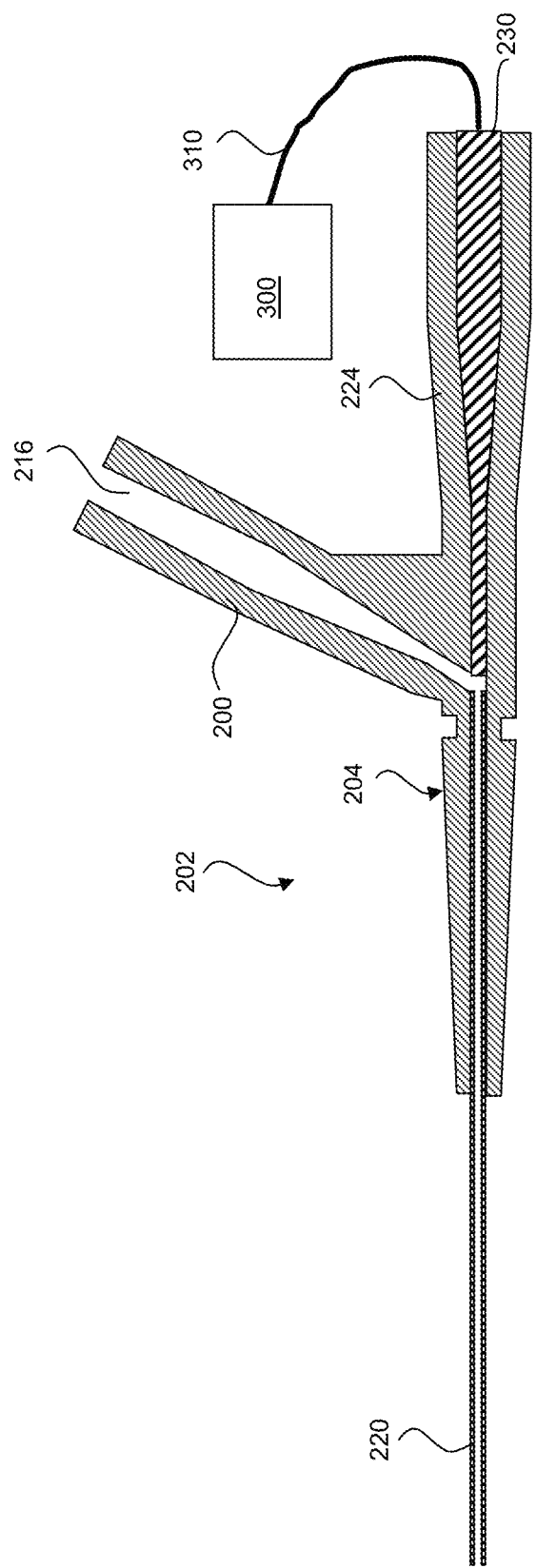

STERILIZABLE INDWELLING CATHETERS

STATEMENT OF RELATED APPLICATIONS

The present application is a continuation of U.S. patent application Ser. No. 11/879,537, filed Jul. 18, 2007, entitled "Sterilizable Indwelling Catheters", the disclosure of which is hereby incorporated by reference in its entirety, which claims the benefit of U.S. Provisional Patent Application Ser. No. 60/839,948, filed Aug. 24, 2006, entitled "Sterilizable Indwelling Catheters", the disclosure of which is hereby incorporated by reference in its entirety.

BACKGROUND OF THE INVENTION

In current medical practice, it is commonly necessary to introduce catheters into subjects for various purposes. For example, catheters may be introduced for purposes of delivering fluids, such as blood, glucose solutions, medications, diagnostic agents, and so forth, to the subject. Catheters may also be introduced for purposes of withdrawing bodily fluids such as blood from the subject.

SUMMARY OF THE INVENTION

According to an aspect of the invention, an indwelling catheter is provided which comprises a catheter shaft. The catheter either comprises a light source or is adapted to receive light from a light source, and is configured such that light is transmitted from the light source into the catheter shaft. Moreover, the catheter shaft is formed of a polymeric material that transmits a quantity of light from the light source that is effective to inactivate microorganisms on a surface of the catheter shaft upon activation of the light source.

According to another aspect of the invention, a sterilization method is provided, which comprises activating the light source while the catheter is inserted in a subject.

An advantage of the present invention is that microorganisms may be inactivated without removing the catheter from the subject.

These and other aspects, embodiments and advantages of the present invention will become immediately apparent to those of ordinary skill in the art upon reading the disclosure to follow.

BRIEF DESCRIPTION OF THE DRAWINGS

FIG. 1A is a schematic perspective view of an indwelling catheter, in accordance with an embodiment of the invention.

FIG. 1B is a schematic cross-sectional view of the catheter of FIG. 1A, in accordance with an embodiment of the invention.

FIG. 1C is a schematic cross-sectional view of the catheter of FIGS. 1A and 1B, upon insertion of a light emitting component, in accordance with an embodiment of the invention.

FIG. 2A is a schematic perspective view of an indwelling catheter, in accordance with an embodiment of the invention.

FIG. 2B is a schematic cross-sectional view of the catheter of FIG. 2A, in accordance with an embodiment of the invention.

FIG. 2C is a schematic cross-sectional view of the catheter of FIGS. 2A and 2B, upon insertion of a light emitting component, in accordance with an embodiment of the invention.

FIG. 3A is a schematic cross-sectional view of an indwelling catheter, in accordance with another embodiment of the invention.

FIG. 3B is a schematic cross-sectional view of the catheter of FIG. 3A upon insertion of a light emitting component, in accordance with an embodiment of the invention.

FIGS. 4 and 5 are schematic perspective views of indwelling catheters, in accordance with other embodiments of the invention.

FIG. 6A is a schematic perspective view of an indwelling catheter, in accordance with an embodiment of the invention.

FIG. 6B is a schematic cross-sectional view of the catheter of FIG. 6A, in accordance with an embodiment of the invention.

FIGS. 7-9 are schematic perspective views of indwelling catheters, in accordance with still other embodiments of the invention.

DETAILED DESCRIPTION

Figure 9:
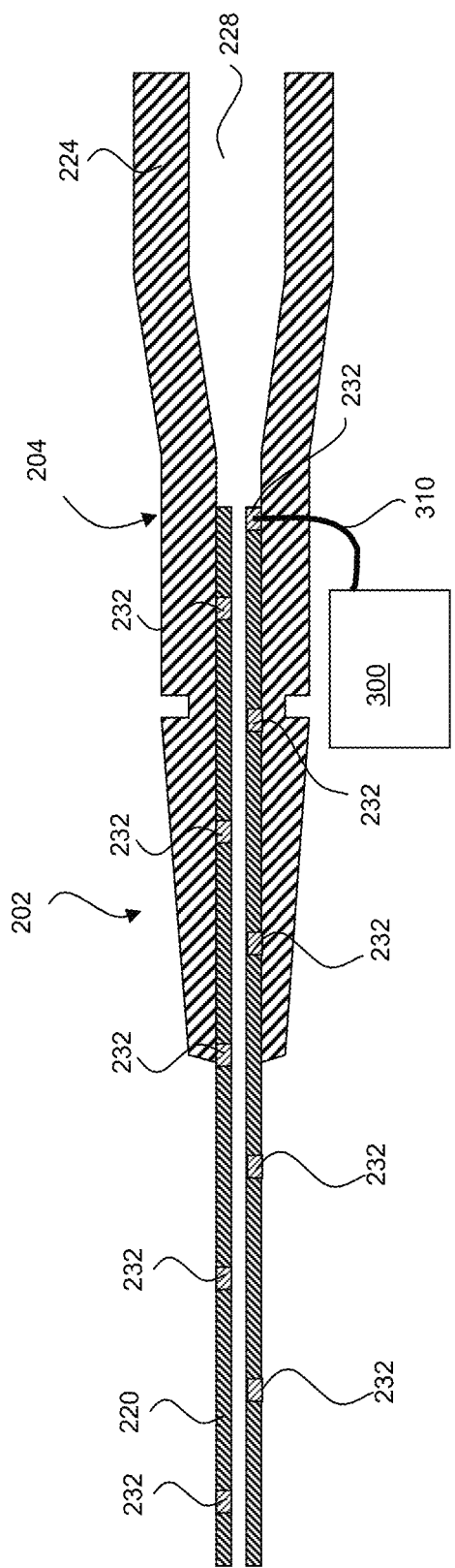

As used herein, a "catheter" is a medical device that includes a flexible shaft, which contains one or more lumens, and which may be inserted into a subject (e.g., a vertebrate subject, for instance, a mammalian subject such a human, dog, cat, horse, etc.) for introduction of fluids, for removal of fluids, or both. Catheters benefiting from the present invention include both acute and chronic catheters.

A catheter may further include various accessory components, for example, molded components, over-molded sub-assemblies, connecting fittings such as hubs, extension tubes, and so forth. Various catheter tips designs are known, including stepped tips, tapered tips, over-molded tips and split tips (for multilumen catheters), among others.

Commonly used catheters include peripheral venous catheters, which as the name suggests, are inserted into a peripheral vein, usually in the hand or arm, for the administration of drugs, fluids, etc. These catheters are typically for short term (acute) use, for example, ranging from 1 to 30 days.

A "central venous access catheter" is a catheter that provides access to the central venous circulation system. Central venous access may be achieved by direct puncture of the central venous circulation system, e.g., via the internal jugular vein, subclavian vein or femoral vein. Catheters of this type, known as "central catheters" or "central venous catheters," are relatively short, and can generally remain in place for only a short time (e.g., generally less than 7 days).

Other central venous access catheters have also been developed which can be inserted into peripheral veins (e.g., the antecubital, basilica, or cephalic vein) and advanced to access the central venous system, with the tip commonly positioned in the superior vena cava or right atrium, thus allowing for rapid dilution of infused fluids. These devices avoid difficulties associated with the direct puncture of the central venous circulation system, and they allow for long term (e.g., 180 days or more) and repeated access to a patient's vascular system, thereby avoiding multiple injections and minimizing trauma and pain to the patient.

Specific examples of catheters of this type include so-called peripherally inserted central catheters ("PICCs"), midline catheters, and peripheral catheters. A typical PICC, midline, or peripheral catheter contains a thin, flexible shaft, which contains one or more lumens and which terminates at the proximal end with a suitable fitting, such as a hub or other fitting. The primary difference between these three devices is the length of the tubing, with the peripheral catheter being the shortest and the PICC being the longest. The rationale for different lengths is driven by the type and duration of the therapy a patient is to receive.

Hemodialysis catheters are another important class of central venous access catheters. Hemodialysis catheters are commonly multi-lumen catheters in which one lumen is used to carry blood from the body to a dialysis machine, and another lumen returns blood to the body. Central venous access may be attained by puncture of various major blood vessels, including the internal jugular vein, subclavian vein, or femoral vein.

Central venous access may also be provided via venous access ports. These specialized catheters typically have the three following components: (a) a catheter, (b) a reservoir, typically formed of a metal or polymer, which holds a small amount of liquid and which is connected to the catheter, and (c) a septum, which covers the reservoir and allows access to the reservoir upon insertion of a needle. The reservoir and covering septum are surgically placed under the skin of the chest or arm, and the catheter extends into a central vein.

Because catheters such as those described above are inserted into the vasculature, sterility is of great concern. Moreover, many of these devices may be inserted for long periods, making in vivo sterilization highly desirable.

It is known that microorganisms, such as viruses, bacteria, fungi, protozoa, algae, and so forth can be inactivated (i.e., either killed or prevented from reproducing, e.g., by molecular rearrangement of the microorganism's DNA) using light of various wavelengths, including ultraviolet light of various wavelengths such as ultraviolet-C (UVC) light having a wavelength of 100 to 280 nm, ultraviolet-B (UVB) light having a wavelength 280 to 320 nm, and ultraviolet-A (UVA) light having a wavelength of 320 to 400 nm. For example, UVC light has a very short wavelength and kills bacteria and viruses so well that it is often used to sterilize surfaces. UVB light has also been reported to kill microorganisms. See, e.g., T. S. Gunasekera et al., "Responses of phylloplane yeasts to UV-B (290-320 nm) radiation: interspecific differences in sensitivity," *Mycological Research* (1997) 101: 779-785. Microorganisms can also be inactivated indirectly, for example, by triggering photosensitizers (also called photodynamic agents) that kill or inactivate the microorganisms. Many of these photosensitizers can be activated by visible, near-infrared or near-ultraviolet light.

Any suitable photosensitizer may be used in conjunction with the present invention, so long as it is effective for inactivating microorganisms under illumination and is not unduly unsafe for the subject. Combinations of photosensitizers may also be employed, for example, to broaden the spectrum of microorganisms that can be inactivated. Suitable photosensitizers may be selected from suitable members of the following known photosensitizers, among others: various dyes, including thiazine dyes such as phenothiazine dyes (e.g., methylene blue, dimethyl methylene blue, new methylene blue n, neutral red, toluidine blue o, thionine, azure c, etc.), acridine dyes (e.g., acridine orange, acridine yellow, proflavin, etc.), coumarin dyes (e.g., thiocoumarin, etc.), xanthene dyes (e.g., eosin, fluorescein, rose bengal, etc.), phenazines (e.g., neutral red, etc.), phenoxaziniums (e.g., brilliant cresyl blue, etc.), aromatic carbonyl compounds (e.g., acetonaphthone, acetophenone benzophenone, etc.), condensed aromatic compounds (e.g., anthracene, naphthalene, pyrene, rubrene, etc.), crystal violet, fluorene derivatives (e.g., fluorine, fluorenones, etc.), psoralens, naphthalocyanines, porphyrin and benzoporphyin derivatives (e.g., copper porphyrin, zinc tetraphenylporphyrin tetrasulfonate, and chlorins such as 5,10,15,20-tetrakis(m-hydroxyphenyl)chlorine), phthalocyanines (e.g., pthalocyaninetetrasulfonic acid as well as zinc-, aluminium- or silicon-phthalocyanines, which may be sulfonated, including aluminium phthalocyanine monosulfonates (A1PcS), aluminium phthalocyanine disulfonates (A1PcS2), aluminium phthalocyanine trisulfonates (A1PcS3) or aluminium phthalocyanine tetrasulfonates (A1PcS4)), thioketones, and the like, as well as mixtures thereof. Those skilled in the art will recognize that sensitizers other than those listed above can be employed so long as the sensitizer functions adequately to inactivate microorganisms under illumination and is not unduly unsafe to the subject. Further information regarding photosensitizers can be found, for example, in U.S. Patent Application No. 2003/0194433, which is hereby incorporated by reference.

One or more photosensitizers may be incorporated into the devices of the invention for release therefrom, one or more photosensitizers may be introduced through the device (i.e., though a catheter lumen), and/or one or more photosensitizers may be introduced independent of the device (e.g., orally, nasally, rectally, vaginally, transdermally, by injection, etc.) such that it is present in the vicinity of the catheter at the time of illumination.

Light sources which are capable of emanating light in the infrared, visible and/or ultraviolet spectra are widely available commercially and include solid-state and non-solid-state devices, such as lasers, light emitting diodes, fluorescent lamps, incandescent lamps and gas discharge lamps, among others. A single light source or an array of light sources may be employed in conjunction with the medical devices of the invention. The light source(s) may be integrated into the medical device. Alternatively, the light source (s) may be optically coupled to the device, for example, either directly or via a light guide.

Light guides include liquid light guides and solid light guides. Liquid light guides generally have a flexible outer sheath and a light-conducting liquid core. They are commonly sealed with quartz windows that can be made transparent to a range of wavelengths. Liquid light guides have little luminous loss over distance and particularly well suited for the transmission of UV light. Solid light guides include, for example, light transmitting cylinders and rods such as optical fibers. A common example of a solid light guide is a fiber optic bundle. Typically, the fibers at each end of the bundle are compressed, cut perpendicular to the axis of the fibers, and polished to permit light to efficiently pass into and out of the bundle. Fiber optic light guides are suitable for the transmission of light in the ultraviolet (e.g., where quartz fibers are employed), visible and near-infrared ranges.

Figure 10C:
FIGS. 10A-10C are perspective views of various known optical couplers.
Figure 10B:
Figure 10A:
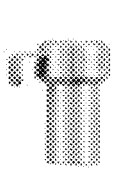
Figure 11C:
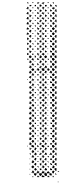
FIGS. 11A-11C are perspective views of various known optical cable end fittings.
Figure 11B:
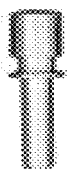
Figure 11A:

Medical devices such as endoscopes commonly employ light emitting components, such as light sources and light guides, for introducing light into the subject and various coupling designs are available, which readily allow the connection and disconnection of light emitting components to and from the device. For example, couplers and end fittings for optical cables, which allow for efficient coupling of light to and from the optical cables, are presently known in the medical arts including those available from Codman, Fuji, Pentax, Pilling, Storz, and Wolf, among others. For example, a Codman/Acmi coupler (female) and end fitting (male) are illustrated in FIGS. 10A and 11A, respectively, a Storz coupler and end fitting are illustrated in FIGS. 10B and 11B, respectively, and a Wolf/Dionics/Medicon coupler and end fitting are illustrated in FIGS. 10C and 11C, respectively. Of course other designs, including other unthreaded and threaded designs, including luer, subminiature, press fit, and bayonet type couplings, among others, may be employed.

Light coupling efficiency may also be increased by matching the refractive index of the material of the light emitting component (e.g., the light source, light guide, etc.) with the material of the medical device (e.g., catheter tube, the hub, etc.) at the point where the light is transmitted into the device. Moreover index matching fluids or gels may be provided between these materials to further improve optical coupling.

As noted above, the medical devices of the present invention typically comprise a shaft that contains one or more lumens (e.g., a tube, multilumen extrusion, etc.), which is introduced into a patient for either short or long term residency.

In accordance with an aspect of the present invention, the material that is selected to form the shaft is substantially transparent to the light wavelength of interest. By "light wavelength of interest," is meant a light wavelength that is capable of inactivating one or more types of microorganism, either directly (e.g., UVC light) or indirectly (e.g., in conjunction with a photosensitizer). By "substantially transparent" is meant that the material is sufficiently transparent to the light wavelength of interest to transmit a quantity of light that is effective to inactivate the one or more types of microorganism, either in all or a portion of the shaft (e.g., the vulnerable portion of the catheter lying proximal to the opening the patients skin, e.g., within 1 cm of the opening).

Suitable shaft materials for this purpose may be selected from (a) various grades of elastomers such as polyurethanes (e.g., polyether- and polycarbonate-based thermoplastic polyurethanes, for instance, Tecoflex 93A polyether-based thermoplastic polyurethane available from Thermedics Polymer Products, Wilmington, Mass., USA, among others) and polyether block amides, among others, (b) fluoropolymers such as fluorinated ethylene polypropylenes (FEP), terpolymers of tetrafluoroethylene, hexafluoropropylene and vinylidene fluoride (THV), perfluoroalkoxy (PFA), polytetrafluoroethylenes (PTFE), polyvinylidene fluorides (PVDF), and Teflon® AF, among others, (c) amorphous polymers such as polycarbonates, acrylic polymers, and polystyrenes, among others, and (d) specially processed semi-crystalline polymers such as polyethylene terephthalates (PET) and polyamides, among others.

Shafts are commonly formed by extrusion, for example, either thermoplastic extrusion or thermoset extrusion as is well known in the catheter art. Moreover, coating processes such as solvent casting may also be employed.

In some embodiments a coating is provided on the catheter shaft. Such a coating may comprise, for example, one or more photosensitizers, which are activated upon exposure to light at the wavelength of interest. In certain of these embodiments, the photosensitizer is immobilized in the coating. In other embodiments, the photosensitizer is slowly released from the coating.

The present invention now will be described more fully hereinafter with reference to the accompanying drawings, in which certain specific embodiments of the present invention are shown. This invention may, however, be embodied in a variety of different forms and should not be construed as so limited.

Referring now to FIGS. 1A and 1B a hub assembly 202 is shown which includes a hub portion 204 having a proximal end and a distal end. At the proximal end of the hub portion 204 is a port 224. Various port designs are known in the art and can include various connector designs such as threaded, luer, subminiature, press fit, and bayonet type connectors, among others. A lumen 228 extends longitudinally through the hub portion. An end of a hollow shaft 220 (i.e., a catheter tube) extends through a passage 222 at the distal end of the hub portion 204 and into the lumen 228 of the same.

As is typical, port 224 allows external fluids such as blood, glucose solutions, medications, diagnostic agents, and so forth, to be delivered to the patient and/or allows bodily fluids such as blood to be withdrawn from the patent.

Moreover, in the embodiment of the present invention shown, light having a wavelength of interest is introduced into the catheter tube 220 via port 224, for example, by inserting a light emitting component 230 (e.g., a light source, a light guide conveying light from a light source, etc.) into the port 224 as shown in FIG. 1C. Once in the position shown, light emitted from the distal end of the light emitting component 230 enters the proximal end of the catheter tube 220. The light travels through the catheter tube 220 and is emitted from both its inner (luminal) and outer (abluminal) surfaces, whereupon it inactivates microorganisms, for example, either directly or with the assistance of a photosensitizer as discussed above.

A multiport hub assembly 202 is illustrated in FIGS. 2A and 2B. As in FIGS. 1A and 1B, the hub assembly 202 includes a hub portion 204, having a port 224 and a lumen 228 extending longitudinally through the hub portion 204. The assembly 202 further includes a hollow shaft 220 (i.e., a catheter tube) which extends through a passage 222 at the distal end of the hub portion 204 and into the lumen 228 of the same. The hub portion 204 of FIGS. 2A and 2B, however, further includes an angled port 200. Angled port 200 defines a lumen 216 extending therethrough, which interconnects with lumen 228 extending through hub 204.

Analogous to FIG. 1C, light having a wavelength of interest may be introduced into the assembly 202 via port 224, for example, by inserting a light emitting component 230 into the port 224 as shown in FIG. 2C. Because the assembly 202 has two ports 200, 224, the light emitting component 230 can permanently occupy the port 224, without losing the catheter's ability introduce and/or withdraw fluids into and from the subject (via port/lumen 200/216). For example, a hub assembly 202 is shown in FIG. 8, which has an integrated light source 230 (e.g. an LED, LED array, laser, laser array, etc.), which is supplied with power from power source 300 via line 310.

In other embodiments, such as that illustrated in FIGS. 3A and 3B, light having a wavelength of interest may be introduced into the assembly 202 via angled port 200, for example, by inserting a light emitting component 230 into the port 200 as shown in FIG. 3B. As with the devices of FIGS. 2A-2C, because the assembly 202 has two ports 200, 224, the light emitting component can permanently occupy the port 200.

FIG. 4 illustrates a simplified version of FIG. 3B, wherein light having a wavelength of interest is introduced into the assembly 202 by temporarily inserting a light emitting component 230 into a simple aperture 204a formed in the side of the hub portion 204.

An analogous hub assembly 202 is shown in FIG. 7, which has an integrated light source, which is supplied with power from power source 300 via line 310.

FIG. 5 illustrates a hub assembly 202, which includes a hub portion 204, having a port 224 and a lumen 228 extending longitudinally through the hub portion 204, as well as a hollow shaft 220 (i.e., a catheter tube) which extends through a passage 222 at the distal end of the hub portion 204 and into the lumen 228 of the same. The hub portion 204 further includes a perpendicular port 200, into which a light emitting component 230 may be temporarily or permanently inserted.

FIGS. 6A and 6B illustrate an embodiment wherein an optical coupler 206, for instance, like that of FIG. 10C, is integrated into the side of the hub portion 204. Such an optical coupler may be used, for example, to temporarily accommodate a light guide having an end fitting like that illustrated in FIG. 11C.

Yet another embodiment of the invention is illustrated in FIG. 9, which illustrates a hub assembly 202 that includes a hub portion 204, having a port 224 and a lumen 228 extending longitudinally through the hub portion 204, as well as a hollow shaft 220 (i.e., a catheter tube) which extends through a passage at the distal end of the hub portion 204 and into the lumen 228 of the same. A plurality of light sources 232 (e.g., LEDs) are embedded within the hollow shaft 220. These light sources 232 are electrically interconnected and powered by a power source 300 via line 310.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of sterilizing a catheter, comprising:
   introducing a catheter comprising a catheter shaft into a patient;
   wherein the catheter shaft projects from a hub;
   wherein the hub includes a lumen contiguous with a lumen of the catheter shaft;
   wherein a light source is receivable within the lumen of the hub and configured to transmit light onto a proximal end of the catheter shaft;
   wherein the catheter shaft is formed of a polymeric material that transmits a quantity of light through the catheter shaft that is effective to inactivate microorganisms on an external surface along a length of the catheter shaft;
   introducing, with the catheter shaft within the patient, the light source into the lumen of the hub and proximal to the lumen of the catheter shaft; and
   activating the light source while the light source remains proximal to the lumen of the catheter shaft and the catheter is within the patient.

2. The method of claim 1, further comprising introducing a photosensitizer to the patient prior to or concurrent with activating the light source.

3. The method of claim 1, wherein the catheter further comprises a photosensitizer.

4. The method of claim 3, wherein the photosensitizer is a coating on the catheter shaft.

5. The method of claim 3, wherein the photosensitizer is a dye.

6. The method of claim 3, wherein the photosensitizer is selected from thiazine dyes, acridine dyes, coumarin dyes, xanthene dyes, phenoxaziniums, phenazines, aromatic carbonyl compounds, condensed aromatic compounds, fluorene derivatives, psoralens, naphthalocyanines, porphyrin, thioketones and combinations thereof.

7. The method of claim 1, wherein the catheter shaft comprises a thermoplastic or a thermoset polymer material.

8. The method of claim 1, wherein the catheter shaft comprises a polymer material selected from polycarbonates, acrylic polymers, polystyrenes, polyethylene terephthalates, polyamides, polyurethanes, polyether block amides, fluoropolymers, and combinations thereof.

9. The method of claim 1, wherein the light source is selected from a laser, a laser array, a light emitting diode, and a light emitting diode array.

10. A method of sterilizing a catheter, comprising:
    introducing a catheter into a patient, the catheter including a catheter shaft with a catheter shaft lumen and a hub with a hub lumen, the catheter shaft projecting from a distal end of the hub and comprising a light transmitting material, the hub lumen configured to receive a light source;
    introducing, with the catheter within the patient, the light source into the hub lumen and proximal to the catheter shaft lumen, the light source configured to transmit light into the catheter shaft;
    activating the light source while the catheter shaft lumen of the catheter shaft remains unobstructed by the light source and the catheter is within the patient; and
    transmitting an effective quantity of light from the light source through the catheter shaft to inactivate microorganisms on an external surface along a length of the catheter shaft.

11. The method of claim 10, wherein the catheter is configured such that light is transmitted from the light source into the lumen of the catheter shaft.

12. The method of claim 10, wherein the catheter is configured such that light is transmitted through a wall of the catheter shaft.

13. The method of claim 10, wherein the light source is selected from a laser, a laser array, a light emitting diode, and a light emitting diode array.

14. The method of claim 10, wherein the catheter is an indwelling catheter.

15. The method of claim 10, further comprising introducing a photosensitizer to the patient prior to or concurrent with activating the light source.

16. The method of claim 10, wherein the catheter further comprises a photosensitizer.

* * * * *